United States Patent [19]

Rosevear et al.

[11] 4,336,161

[45] Jun. 22, 1982

[54] COMPOSITE MATERIALS COMPRISING DEFORMABLE XEROGEL WITHIN THE PORES OF PARTICULATE RIGID SUPPORTS USEFUL IN CHROMATOGRAPHY

[75] Inventors: Alan Rosevear, Faringdon; Patrick Mattock, Botley, both of England

[73] Assignee: United Kingdom Atomic Energy Authority, London, England

[21] Appl. No.: 85,201

[22] Filed: Oct. 16, 1979

Related U.S. Application Data

[60] Division of Ser. No. 858,798, Dec. 8, 1977, which is a continuation-in-part of Ser. No. 750,706, Dec. 15, 1976, abandoned.

[30] Foreign Application Priority Data

Dec. 15, 1975 [GB] United Kingdom ............... 51345/75
Dec. 15, 1976 [GB] United Kingdom ............... 52432/76
Dec. 16, 1976 [GB] United Kingdom ............... 52433/76

[51] Int. Cl.$^3$ .................. B01J 20/32; B01J 20/26; B01J 20/22; B01D 15/08
[52] U.S. Cl. ............................. 252/426; 55/67; 210/635; 210/656; 260/122; 252/428; 252/430; 252/451; 252/455 R; 435/176; 435/178; 435/181

[58] Field of Search ............... 252/428, 430, 449, 451, 252/426; 260/121, 122; 210/31 C, 635, 656; 55/67; 435/174–182

[56] References Cited

U.S. PATENT DOCUMENTS

| | | | |
|---|---|---|---|
| 3,403,109 | 9/1968 | Colgan et al. ...................... | 252/451 |
| 3,442,819 | 5/1969 | Herbert .............................. | 252/428 |
| 3,922,432 | 11/1975 | Renn ................................. | 210/31 C |
| 3,941,718 | 3/1976 | Barabas ............................. | 252/428 |
| 3,943,072 | 3/1976 | Thomson .......................... | 252/437 |
| 3,947,352 | 3/1976 | Cuatrecasas et al. ............. | 210/31 C |
| 3,954,678 | 5/1976 | Marquisee ........................ | 252/451 |
| 3,960,720 | 6/1976 | Porath et al. ...................... | 252/426 |
| 4,000,098 | 12/1976 | Hofstee et al. ...................... | 210/24 |
| 4,016,149 | 4/1977 | Travis et al. ....................... | 260/122 |
| 4,045,353 | 8/1977 | Kosaka et al. ................... | 210/198 C |

FOREIGN PATENT DOCUMENTS

1537086 12/1978 United Kingdom .

Primary Examiner—P. E. Konopka
Attorney, Agent, or Firm—Larson and Taylor

[57] ABSTRACT

The invention discloses a composite material comprising a deformable gel retained within the pores of a porous rigid support material. The deformable gel comprises an affinity chromatography agent such that the composite material has affinity chromatography properties.

9 Claims, No Drawings

COMPOSITE MATERIALS COMPRISING DEFORMABLE XEROGEL WITHIN THE PORES OF PARTICULATE RIGID SUPPORTS USEFUL IN CHROMATOGRAPHY

This is a division of co-pending application Ser. No. 858,798, filed Dec. 8, 1977, which was a continuation-in-part of application Ser. No. 750,706, filed Dec. 15, 1976 now abandoned.

The present invention relates to composite materials.

According to one aspect of the present invention, there is provided a composite material comprising a deformable gel retained within the pore structure of a porous rigid support material.

By "deformable gel" we mean a gel which itself is a non-rigid material (e.g. a xerogel). Such deformable gels include organic polymeric materials and certain inorganic materials, for example, silicic acid.

Preferably, the porous rigid support material is in the form of discrete porous particles having an interconnected pore structure (for example those particles of inorganic material which may be prepared in accordance with Application Ser. No. 455,948, now U.S. Pat. No. 3,943,072.

The term "aerogel" has been used in the art to describe a rigid, preformed matrix containing pores and this term and the term "xerogel" are discussed in "An Introduction to Permeation Chromatography" by R. Epton and C. Holloway issued by Koch-Light Laboratories Ltd.

In one embodiment of the present invention, the deformable gel is an organic polymeric material chosen so as to be interactive with chemical species (e.g. macromolecules such as proteins) in solution so that the composite material is capable of sorbing chemical species from solution. The organic polymeric material can be chosen such that the interaction is predominantly chemical (for example ion exchange) or predominantly physical (for example possessing the ability to delay permeation of chemical species physically as in the case of gel filtration media and molecular sieve materials).

Examples of organic polymeric materials which can be used in accordance with the present invention are celluloses and polysaccharides to which ion exchange groupings can be, or have been, attached and gel filtration celluloses.

In another embodiment of the present invention an affinity chromatography agent is, or is part of, the deformable gel such that the composite material is a composite material having affinity chromatography properties.

By "affinity chromatography agent" we mean a substantially insoluble material having ligands capable of selectively sorbing a given chemical component from a mixture of components in a fluid substance (e.g. in solution), the sorbing being a result of interaction between a specific site or sites on the given chemical component with a particular site or sites on the ligand. Accordingly when a material is said to have "affinity chromatography properties" it means that it is capable of selectively sorbing a given chemical component from a mixture of components in a fluid substance by means of interaction between a particular site or sites on ligands on the material and a specific site or sites on the given chemical component.

Affinity chromatography agents have been used particularly in the separation and purification of water soluble components where the nature of the interaction between agent and component is of a biochemical nature or involves biochemical molecules. Techniques of affinity chromatography are described in "Methods in Enzymology" Vol. 34. Edited by W. B. Jakoby and M. Wicheck, Academic Press (1975).

In a further embodiment of the present invention an empholyte agent is, or is part of, the deformable gel such that the composite material is an ampholyte material.

By "ampholyte agent" we mean a substance which contains both insoluble basic and acidic chemical groups. The ratio of these two types of insoluble groups determines the net charge on the agent and thus the pH at which it has maximum capacity for protons (i.e. the maximum buffering capacity). Accordingly by "ampholyte properties" we mean having the ability to buffer hydrogen ion concentrations.

(For biochemical applications the pH at which hydrogen ion concentration buffering is required is typically between 2.5 and 10.5 (i.e. at "non-extreme" pH values.)

In view of the foregoing statements in this specification it will be appreciated that the present invention is concerned with the provision of a rigid "skeleton" having dimensional stability as a support for a non-rigid deformable gel. Thus deformable gels which have, or can be treated to have, useful interactive properties (e.g. ion exchange, gel filtration, affinity chromatography or ampholyte properties), but which are difficult or inconvenient to handle because of their non-rigid nature (e.g. hydrogels which will undergo dimensional changes when subjected to pressures normally found in column operations (e.g. up to ~3 atmospheres) and deform to cause an increase in back pressure) are incorporated into a composite material of the present invention which, due to the rigidity imparted by the porous rigid support material "skeleton", can be handled and used more easily.

Thus, where the composite material comprises, for example, discrete porous particles with a deformable gel retained therein, the composite materials can be loaded into, and used, conveniently in column systems.

Thus, for example, ion exchange celluloses and ion exchange polysaccharides hereinbefore mentioned have useful sorptive capacity for proteins, but due to their non-rigid, deformable nature are not easily handled nor used in column separation apparatus. We have found, however, that if celluloses or polysaccharides of this type are retained in accordance with the invention in discrete porous particles (for example porous particles of a natural earth (such as celite or Kieselguhr) made in accordance with the U.S. Patent hereinbefore mentioned, the composite material comprising cellulose, or polysaccharide, and rigid support material have been found to possess desirable properties. Thus, the particles of composite material tend to settle readily in aqueous media and can be used to form columns having good flow properties. Also, the particles of composite material tend to be stable and not liable to release "fines". The particles of composite material can therefore be introduced into columns and used to function chromatographically with regard to systems containing selected chemical species (for example macromolecules such as proteins).

Similarly, we have found that if deformable gels having affinity chromatography properties or ampholyte properties are retained in accordance with the invention in discrete porous particles (for example porous particles of a natural earth (such as celite or Kieselguhr) made in accordance with the U.S. Patent hereinbefore mentioned, the composite material comprising deformable gel having affinity chromatography properties or ampholyte properties, and rigid support material possess the desirable properties hereinbefore mentioned. Thus, the particles of composite material tend to settle readily in aqueous media and can be used to form columns having good flow properties. Also, the particles of composite material tend to be stable and not liable to release "fines".

Thus, the particles of composite material having affinity chromatography properties or ampholyte properties can be introduced into columns and used to function chromatographically with regard to systems containing selected chemical species (for example macromolecules such as proteins).

Ampholyte materials have weak ion exchange properties and therefore will be capable of sorbing macromolecules, such as proteins, from solution.

According to another aspect, the present invention provides a method for preparing a composite material of a deformable gel retained in the pore structure of a porous rigid support material which comprises introducing a precursor for the gel into the pore structure of a porous rigid support material and treating the precursor to form and retain the deformable gel in the pore structure.

It will be appreciated that the majority of the deformable gel will be present in the internal pore structure of the porous rigid support material, but also it should be noted that some gel may be formed on the surface of the support material.

An important feature of the invention is that there is produced a composite material in which there is the minimum of deformable gel outside of the internal pore structure of the porous rigid support material. Thus, where the porous rigid suppot material is in the form of discrete porous particles there is a minimum of deformable gel formed between the particles, and substantially all of the deformable gel formed is retained by the particles with the majority of the deformable gel being in the internal pore structure thereof, so that the resulting composite material is in the form of discrete particles such as to aid, inter alia, handling, column packing and column operation.

Loosely adhering deformable gel may be removed from the particles of composite material by washing and, if necessary mechanical means (e.g. sieving).

To assist in maximising the amount of the deformable gel retained in the pore structure of the porous rigid support material where, in accordance with an embodiment of the method of the invention a solution of precursor is contacted with the porous rigid support material to introduce precursor into the pore structure, we prefer that the volume of the solution of precursor contacted with the suppot material (e.g. by soaking the support material in the solution) is approximately equal to the volume required to fill the pore structure. It will be appreciated that to minimise the amount of deformable gel formed outside the pore structure the volume of the solution should not exceed the volume required to fill the pore structure.

It will be appreciated that in general the viscosity of the solution of the precursor should be such that it does not prevent uptake thereof by the support (e.g. by capillary action).

Also we prefer that the volume of any reagent solutions used to treat the precursor in the pore structure to form a gel is not substantially in excess of that required to immerse the porous rigid support material.

The deformable gel as formed by treating the precursor may be itself inter-active towards chemical species. Alternatively the gel can be formed and retained in the pore structure of the support material and subsequently further treated to make it chemically inter-active towards chemical species; i.e. the gel can be treated to make it chemically inter-active in situ in the porous rigid support material (e.g. by introducing chemical groups (such as amino or carboxylic acid) into a retained cellulose or a polysaccharide gel to form an ion exchange cellulose gel or an ion exchange polysaccharide gel composite material by known techniques.

Furthermore, the gel may be treated to couple a biologically active substance (e.g. an enzyme) to the gel (e.g. cellulose) by known techniques. Thus, for example, an enzyme may be coupled to a cellulose gel by the carbonate link described by J. F. Kennedy, S. A. Barber and A. Rosevear in J. Chem. Soc., Perkin Transactions I, (1973) p 2293.

[The term "biologically active substance" as used in this specification embraces inter alia proteinaceous substances which are biologically active per se and those which are not but can be activated to make them biologically active.

Furthermore, it is to be understood that the term "biologically active substance" embraces inter alia those substances capable of participating in specific interactions, such substances including, for example, substances of biological origin and those which act on living organisms. Substances of synthetic origin which can participate in reactions involving specific interactions analogous to those which can occur with naturally occurring substances are also embraced within the term "biologically active substance".]

As further alternatives the gel may be chosen to have or treated to have affinity chromatography properties or ampholyte properties.

Thus in one embodiment of the method of the present invention a composite material of a deformable gel having affinity chromatography properties retained within the pore structure of a porous rigid support material is prepared by introducing a precursor for the gel into the pore structure of a porous rigid support material and treating the precursor to form and retain the deformable gel in the pore structure.

In another embodiment of the present invention a composite material of a deformable gel having affinity chromatography properties retained within the pore structure of a porous rigid support material, is prepared by a method which includes the step of treating an inactive deformable gel retained within the pores of a porous rigid support material to impart affinity chromatography properties to the inactive deformable gel.

In a further embodiment of the method of the present invention a composite material of a deformable gel having ampholyte properties retained within the pores structure of a porous rigid support material is prepared by introducing a precursor for the gel into the pore structure of a porous rigid support material and treating the precursor to form and retain the deformable gel in the pore structure.

In yet a further embodiment of the present invention a composite material of a deformable gel having ampholyte properties retained within the pore structure of a porous rigid support material is prepared by a method which includes the step of treating an inactive deformable gel retained within the pores of a porous rigid support material to impart ampholyte properties to the deformable gel.

It will be appreciated that by "inactive deformable gel" in relation to the preparation of composite materials having affinity chromatography properties or ampholyte properties respectively we mean that a deformable gel having little or no useful affinity chromatography properties or ampholyte properties respectively.

To produce a composite material having affinity chromatography properties the inactive deformable gel can be treated to have affinity chromatography properties by modifying the inactive gel or by adding further species (e.g. ligands) thereto.

The inactive deformable gel may be a neutral polyol (e.g. P.V. Alcohol or agarose) or a gel which can be treated to be non-sorptive per se.

Where the affinity chromatography agent is part of the deformable gel, it will be appreciated that other constituents of the deformable gel in the finished composite should not have sorptive properties, since such properties could compete with the affinity chromatography agent.

An example of a composite material in accordance with the present invention is discrete porous particles of celite (prepared in accordance with BP No. 1421531 (U.S. Pat. No. 3,943,072)) having retained within the pore structure thereof an agarose gel to which has been coupled the dye Cibacron Blue 3 G-A (ex Ciba-Geigy). Cibacron Blue 3G-A dye is an affinity chromatography ligand capable of retaining proteins (e.g. albumin) from human plasma, the structure of this dye is given hereinafter.

Cibracron Blue 3G-A is a group specific ligand and is known to interact specifically with the nucleotide binding site of certain enzymes (e.g. kinases and dehydrogenases). It will be appreciated that other affinity chromatography ligands may be coupled to the deformable gel within the porous rigid support material. Examples of such ligands are described in "Methods in Enzymology" Volume 34 hereinbefore mentioned.

Examples of organic polymeric materials which can be formed as inactive deformable gels in the pore structure of a porous rigid support material and subsequently treated to add further species thereby to impart affinity chromatography properties are: polysaccharide gels (e.g. agarose gels and cellulose gels) and synthetic polymer gels such as polymers of acrylates and polyvinyl alcohol polymer gels.

Cibracron Blue 3G-A is a group specific ligand and is known to interact specifically with the nucleotide binding site of certain enzymes (e.g. kinases and dehydrogenases).

The structure of Cibacron Blue 3G-A is as follows:

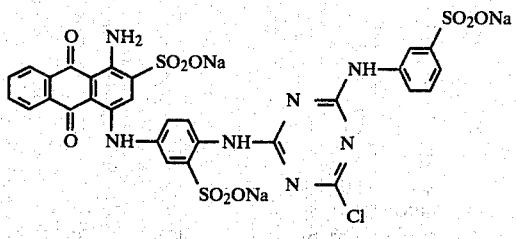

To produce an ampholyte composite material the inactive deformable gel can be treated to have ampholyte properties by modifying the inactive gel or by adding further species (e.g. acids and bases) thereto. For example ampholyte properties may be imparted to an inactive deformable gel (e.g. a cellulose or an agarose gel) by treating the inactive gel after formation in the pore structure to introduce acidic and basic groups. Another example is to form in the pore structure an inactive gel which contains either an acidic or basic component of an ampholyte and to treat the inactive gel to introduce the other component of the ampholyte (e.g. an inactive gel could comprise DEAE dextran (an amine) and acid groups could be added, or the inactive gel could comprise CMC cellulose (an acid) and amine groups could be added.

An example of a composite material in accordance with the present invention is discrete porous particles of celite (prepared in accordance with BP No. 1421531 (U.S. Pat. No. 3,943,072)) having retained within the pore structure thereof an imine/glutamate gel.

Examples of organic polymeric materials which can be formed as insoluble ampholyte gels in the pore structure of a porous rigid support material are: co-polymers of amino acids, acrylic acid derivatives, ethylene imines, acidic polysaccharides and basic proteins.

It will be appreciated that co-polymers of amino acids can provide basic and acidic groups, acrylic acid derivatives and acidic polysaccharides can provide acidic groups, and ethylene imines and basic proteins can provide basic groups in ampholyte gels.

Examples of porous rigid support materials suitable for use in forming composite materials in accordance with the present invention are disclosed in U.S. Pat. No. 3,943,072 hereinbefore mentioned. For example, using one of the discrete porous particle materials disclosed therein, we have prepared discrete particles of composite materials comprising porous rigid particles of celite having cellulose retained thereon and discrete particles comprising porous rigid particles of celite having polysaccharides retained thereon. Furthermore, we have prepared discrete porous particles of composite materials having respectively affinity chromatography properties and ampholyte properties using, by way of example, discrete porous particles of celite as disclosed in British Pat. No. 1421531 (U.S. Pat. No. 3,943,072). Discrete porous particles as described in our aforementioned British (and U.S.) patents and being of materials other than celite, may, of course, be used in accordance with the present invention.

A number of methods may be used to prepare a deformable gel in the pore structure of the porous rigid support material.

Thus, according to one embodiment of the method of the present invention, precursor for a deformable gel can be introduced into the pore structure of the porous rigid support material in solution and the solution in the support material subsequently treated with a precipitating agent to cause precipitation of a deformable gel from the precursor solution.

Where the deformable gel so precipitated in the pore structure of the support material is "inactive deformable gel" (e.g. has no affinity chromotography properties nor ampholyte properties per se) the composite material can be treated to impart affinity chromatography properties or ampholyte properties to the inactive deformable gel in the pore structure.

An example of the immediately foregoing embodiment of the invention is the precipitation (i.e. deposition) of rayon gel in the pore structure by introducing an aqueous solution of the cuprammonium complex of cellulose into the pore structure and subsequently treating the solution retained in the pore structure with dilute mineral acid to cause precipitation of rayon gel in the pores.

This rayon gel can be treated subsequently to formation in the pores to impart affinity chromatography properties or ampholyte properties.

By way of further example a solution of an amine group containing molecule (such as an imine) and an acidic group containing molecule (such as monosodium glutamate) can be introduced into the pore structure of a porous rigid support material by soaking the support material in the solution and subsequently an ampholyte gel, containing both amine groups and acidic groups, produced by precipitation from the solution and cross-linking.

Further examples of precipitation reactions which may be used in carrying out the method of the present invention are (i) the regeneration of cellulose or cellulosic ion exchangers from solutions of the corresponding xanthates (e.g. by decomposition of the xanthates of cellulose, DEAE-cellulose or CMC-cellulose by aqueous mineral acids), (ii) decomposition of a silicate by mineral acid to give silicic acid gel, and (iii) precipitation of acidic polysaccharides with acid or calcium salts.

In another embodiment of the method of the present invention a precursor can be introduced into the pore structure of the porous rigid support material and subsequently polymerized to form a polymer gel in the pore structure (e.g. acrylic acid derivatives may be introduced to the pore structure and subsequently polymerized to give gels of polymers and co-polymers of the derivatives e.g. acrylamide). The polymer gel may be treated as necessary to impart affinity chromatography properties or ampholyte properties.

In a further embodiment of the invention cross-linking of the precursor can be used to form a gel. The cross-linking may be carried out with a chemical cross-linking chemical agent by diffusing the agent into the pore structure in order to react with the precursor. It is very desirable to carry out the cross-linking under conditions such that significant quantities of the precursor cannot diffuse out of the porous rigid support material whilst the cross-linking agent is diffusing into the porous rigid support material. This can be achieved by temporarily retaining the precursor in the support material (e.g. by precipitation) and subsequently treating the precipitated precursor to cross-link it. It will be appreciated that by "temporarily retaining the precursor" we mean that the precursor is "localised" in the support to prevent it diffusing out as the cross-linking agent diffuses in. Where the precursor has been introduced to the porous material in aqueous solution precipitation can be achieved, for example, by contacting the aqueous precursor solution with a water miscible organic solvent (e.g. acetone) capable of removing water from the aqueous solution thereby to precipitate precursor in the pore structure.

For example DEAE-dextran, polysaccharides and neutral polyols can be precipitated from aqueous solution using acetone as the water miscible organic solvent and cross-linked by use of epichlorhydrin. Examples of substances which can be used to produce a deformable gel in a composite material in accordance with the present invention by precipitation and cross-linking are dextran, dextran sulphate, CMC-cellulose, acrylamide, agarose and P.V. alcohol.

Cross-linking agents for use in accordance with the present invention can be for example, epichlorhydrin, bisepoxides, or dihalo compounds for polyols and, for example, dialdehydes for proteins.

Where the precursor, precipitation mechanism and cross-linking agent are such that the cross-linking of the precursor to form the gel is slow in comparison with the rate of precipitation, the precursor and cross-linking agent can be introduced into the pore structure of the porous rigid support material together in one solution (i.e. because precipitation will be effected before cross-linking occurs).

It will be appreciated that the present invention is not limited to composite material which can be used in aqueous solution, and that composite materials can be prepared which may be used in non-aqueous systems.

It will also be appreciated that the deformable gel and porous rigid support material should be substantially insoluble in fluid substances with which they may be contacted in use (e.g. solution to be buffered, solution containing chemical components to be sorbed, feed solutions containing proteins and eluting agents solutions).

Chemical species can be sorbed from a solution by contacting the solution with a composite comprising a deformable gel retained within the pore structure of a porous rigid support material.

The invention also provides a composite material whenever prepared by a method in accordance with the invention.

Also the invention provides a composite material obtainable by a method in accordance with the invention.

A column of an ampholyte material in accordance with the present invention (e.g. in particulate form) may be used for isoelectric focussing in which a particular macromolecule (e.g. a protein) is retained from solution by an ampholyte material which buffers the surrounding solution to the pH at which the macromolecule has no net charge (i.e. its isoelectric point). Under these conditions the particular macromolecule will be selectively retained by the ampholyte material when an electric field is applied to the column and any of the particular macromolecules introduced to the column in solution will concentrate in the ampholyte material.

U.S. Pat. No. 3,943,072 discloses and claims, inter alia, "A method for producing an inorganic material having interconnected porosity throughout the material for the selective retention of predetermined molecules from a fluid substance containing said molecules including the steps of mixing a finely divided, substantially insoluble, sorptive, inorganic material, capable of sorbing the molecules, with a solid fugitive additive to form a mixture, including in the mixture a solvent to dissolve fugitive additive in the solvent, said inorganic material being substantially insoluble in said solvent, forming discrete particles from the mixture, and heating the particles to remove solvent and fugitive additive to produce discrete particles of said inorganic material having an interconnected pore structure throughout said discrete particles providing an extended surface area, the pore size being such as will allow said predetermined molecules in said fluid to permeate the inorganic particles and be sorbed, said inorganic material being substantially unaffected by said heating utilized to effect removal of solvent and fugitive additive." and also claims on inorganic material made by the method claimed in U.S. Pat. No. 3,943,072.

Discrete porous particles (for example those fabricated from a finely divided substantially insoluble, sorptive inorganic material in accordance with U.S. Pat. No. 3,943,072) for use in accordance with the present invention preferably have a porosity of >20% and an interconnected porosity with pores ≧2000 A such as to allow both deformable gel and macromolecules (e.g. proteins or enzymes) to occupy the pores.

"Celite" (Registered Trade Mark) as hereinbefore mentioned is a natural diatomaceous earth produced by Johns-Manville Corporation.

It is believed that porous materials, having dimensional stability such as foam metal and plastic foams can be used as porous rigid support materials in accordance with the present invention.

The invention will now be further described, by way of example only, as follows:

EXAMPLE 1

A composite material was prepared comprising an ion exchange xerogel retained within the pore structure of an aerogel porous rigid support material. An aqueous solution (15 ml) of diethylaminoethyl (DEAE) dextran (15 g/100 ml; ex Pharmacia Fine Chemical) was contacted with, and allowed to soak into the pores of, a porous rigid support material comprising porous celite particles prepared in accordance with British Pat. No. 1421531 (U.S. Pat. No. 3,943,072) (20 ml bed of 350–500μ particles). This was done by adding about 16 ml of solution until all the particles were just covered. The particles were then contacted with acetone (20 ml) whereupon DEAE-dextran was precipitated in the pores from the solution therein.

The particles were agitated to ensure mixing and subsequently the supernatant liquid, comprising acetone and unretained precipitated DEAE-dextran, was poured off.

The particles containing precipitated DEAE-dextran were further treated to cross-link the precursor as follows: acetone (20 ml) was contacted with the particles subsequently epichlorhydrin (1.5 ml) (a cross-linking agent) and triethylamine (4 ml) (a base) were added and, after mixing, the cross-linking reaction was allowed to proceed for 22 hours at ambient temperature.

The particles of composite material (comprising ion exchange xerogel and porous support material) were then washed free of reagents using water and the ion exchange properties investigated.

The particles of composite material were found to remove protein (haemoglobin from a solution containing 5 mg protein per ml. Subsequently the particles which were perceptively brown after taking up protein, were washed to remove unbound protein, and the bound protein subsequently removed, by use of dilute alkali, for assay.

Porous celite particles, (as hereinbefore mentioned) not treated in accordance with the present invention, were contacted with the haemoglobin solution in a control experiment.

The assay results showed that four times as much haemoglobin was recovered from the particles of composite material as from the porous celite particles.

EXAMPLE 2

An essentially similar procedure to that in Example 1 was followed except that in the cross-linking dimethylformamide (4 ml) (a base) was used with the cross-linking agent epichlorhydrin. Assay results showed that three times as much haemoglobin was removed from the composite material produced in this example as from porous celite particles used as a control experiment.

By calcining it was determined that the composite material of Example 2 contained 39% carbohydrate by weight.

EXAMPLE 3

A composite material was prepared comprising a cellulosic xerogel retained within the pore structure of an aerogel porous rigid support material.

An aqueous solution of cuprammonium cellulose (16 ml) was contacted with, and allowed to soak into, the pore structure of a porous rigid support material comprising porous celite particles prepared in accordance with U.S. Pat. No. 3,943,072 (20 ml bed of 350–500μ particles).

Cellulose was precipitated within the pores by rapidly mixing the soaked particles with dilute sulphuric acid (~2N) thereby to give a composite material comprising cellulose gel retained within the porous celite particles. Unbound cellulose was removed by vigorous washing with water.

The composite was found to exhibit gel filtration properties in that it was capable of separating dextran blue from methyl red and cobalt ions from dextran blue.

By calcination it was determined that the composite material of this example contained 1.5% by weight organic material.

EXAMPLE 4

In this Example the composite material prepared in Example 2 was investigated with respect to its ability to sorb protein from solution.

A column (0.5 cm diameter by length 10 cm) was packed with the composite material. The particles settled quickly after pouring and the column was then ready for use.

The column was equilibrated with 5 mM TRIS buffer (pH8) and subsequently haemoglobin dissolved in the same buffer (10 mg 1 ml) was introduced to the column such that haemoglobin was sorbed by the particles of composite material.

Further TRIS buffer was passed through the column and it was noted that a red/brown colour band (of haemoglobin) was retained at the top of the column.

A 0.1 M sodium chloride solution was passed through the column and the haemoglobin band was eluted from the particles.

EXAMPLE 5

A hot aqueous solution of agarose (4% w/v) was mixed with porous celite particles (as disclosed in British Pat. No. 1421531 (U.S. Pat. No. 3,943,072); 400–700μ dia) until the porous particles were completely filled. The mixture was boiled for 5 minutes and excess liquid poured off the particles. The agarose was gelled by pouring the particles into a fluidised bed of cold water.

The agarose in the porous particles was cross-linked as follows:

The particles were washed in 0.5 M caustic soda solution and then reacted with epichlorhydrin (10 ml) in 0.5 M caustic soda (50 ml) for 2½ hrs at 60°. The resulting slurry was agitated at intervals to distribute the epichlorhydrin. The resulting agarose/celite (i.e. celite particles with agarose gel in the pores) particles were washed and stored in water. By drying and pyrolysis at 700°, it was estimated that the composite contained 8.8% by weight organic material.

EXAMPLE 6

A hot aqueous agarose solution (50 ml) and porous celite particles (of the kind used in Example 5) (75 ml) were mixed together and allowed to cool thereby to form an agarose gel within the celite particles. Any agglomerations were broken down by lightly brushing through a 1200μ mesh sieve.

The agarose was then cross-linked by the following procedure:

The agarose-celite composite was added to an emulsion (prewarmed to 60° C.) formed by stirring together 50 ml 1 M NaOH, 10 mls epichlorhydrin and 2.5 g "TWEEN 20" (surfactant).

The composite and emulsion were kept at 60° C. for 2 hours and subsequently the composite was found to contain 10.1% organic material.

EXAMPLE 7

The procedure of Example 5 was followed to produce agarose precipitated in porous celite particles with the exception that the particles were washed with tetrahydrofuran and the cross-linking was carried in a solution of epichlorhydrin (10 ml) and triethylamine (10 ml) in tetrahydrofuran (50 ml) for 3 hours at 20°. The resulting composite contained 7.9% organic material.

EXAMPLE 8

Porous celite particles (of the kind used in Example 5) were soaked in a hot 4% aqueous solution of agarose and an agarose gel precipitated in the particles by dropping the mixture into cold hexane. The agarose was cross-linked as in Example 5. The composite contained 3.2% organic material.

EXAMPLE 9

A composite of agarose and celite particles was prepared as in Example 5 with the exception that cross-linking was achieved with a solution of epichlorhydrin (10 ml) in 0.5 M caustic soda in 1:1 aqueous dimethyl sulphoxide for 2½ hrs at 60°. The organic material content of the particles was 2.7%.

EXAMPLE 10

A solution of egg albumin (100 mg/ml, 15 ml) was soaked into porous celite particles (of the kind described in Example 5) (20 ml) and a solution of 2% tannic acid in water (50 ml) was added to precipitate the albumin. Excess liquid was decanted off and the particles heated to 60° for 2½ hrs to denature the albumin thereby to render it insoluble.

EXAMPLE 11

A solution of acrylamide (3.1 g), +bis acrylamide (0.04 g) in 58 ml of water were degassed and mixed with 0.09 ml of TEMED (NNN'N'-tetramethyl 1:2 diaminoethane). An aqueous solution of ammonium persulphate (3 ml, 15 mg/ml) was added to initiate polymerisation and the solution soaked into porous celite particles (of the kind used in Example 5) (100 ml) in a flask which was purged with nitrogen. The nitrogen blanket was maintained for 20 min when the particles were washed, brushed through a sieve and stored in water.

The organic content was 10.7%.

EXAMPLE 12

A hot aqueous solution of poly vinyl alcohol (10%) was soaked into porous celite particles (of the kind used in Example 5) and the poly vinyl alcohol in the particles precipitated with cold acetone. The particles were washed in 0.5 M caustic soda in acetone/water (3:2), then added to 40 ml of this solvent containing 5 ml of epichlorhydrin and kept at room temperature for 2¼ hrs. The organic content of the composite was 7.0%.

EXAMPLE 13

A mixture of 50 ml of hot 10% aqueous poly vinyl alcohol and porous celite particles (of the kind used in Example 5) (75 ml) were added to cold acetone to precipitate poly vinyl alcohol in the particles. The particles were then reacted with epichlorhydrin (5 ml) and 0.5 M caustic soda in 1:1 aqueous acetone (25 ml) at room temperature for 4½ hrs. The organic content (by pyrolysis) was 9.8%.

EXAMPLE 14

A solution of cellulose acetate in acetone (5 ml), 8.0% was soaked into 10 ml porous celite particles (of the kind used in Example 5) and the cellulose acetate precipitated by adding water (15 ml). The cellulose acetate (ester) was saponified with 10 ml of 1 M caustic soda for 6 hours. The organic content of the composite was 6.3%.

EXAMPLE 15

5 ml of particles of an agarose/celite composite prepared in accordance with Example 5 were covered with a 12.5% solution of titanium chloride in hydrochloric acid and dried overnight in an oven at 45°. The particles were washed and soaked in a solution of amyloglucosidase (A.B.M. LE90) overnight at 5° C. to give a light brown particulate product being a composite of celite, agarose and amyloglucosidase. When asseyed for enzyme activity using thinned starch as the substrate the enzyme bearing composite was found to be 50% more active than a sample of $TiCl_4$ activated celite treated with amyloglucosidase overnight at 4° C.

EXAMPLE 16

An example of an albumin/celite composite described in Example 10 was soaked in a 5% solution of glutaraldehyde for 2½ hrs, washed, covered by a solution of amyloglucosidase (A.B.M. LE 90) and left overnight at 4° C. The activity of the resulting enzyme bearing composite was similar to that of the enzyme bearing composite in Example 15.

EXAMPLE 17

The proportion of the pore volume of the composite materials of Examples 5 and 11 accessible to molecules of different sizes (gel permeation properties) was determined by mixing equal volumes of the particles of composite material and solutions of marker compounds of known M.Wt (1 mg/ml in 1% salt). The particles were shaken with the solutions, centrifuged and the dilution of the marker estimated by measuring the OD of the supernatant solution at 280 nm.

The results are presented in the following table.

| Markers in order | Dilution factor | |
|---|---|---|
| of increasing M.Wt | Agarose/celite | Acrylamide/celite |
| Myoglobin | 1.9 | 2.1 |
| Ovalbumin | 1.7 | 1.7 |
| γ-globulin | 1.6 | 1.3 |
| Blue Dextran | 1.5 | 1.5 |

Note:
The smaller the dilution factor the less of the pore volume is available to that molecule.

EXAMPLE 18

An agarose/celite composite as prepared in accordance with Example 5 (8.8% organic content) was treated to introduce affinity chromatography properties thereto by covalent coupling an affinity chromatography dye to the agarose.

Thus, 5 mls of the composite were washed in water, the water was decanted and 5 ml of water added. The composite was heated to 60° C. and a solution of Cibacron Blue 3G-A in water (4% w/v, 1 ml) was added and the particles and solution mixed. After 15 minutes sodium chloride (0.5 g) was added, the mixture was heated to 90° C. and a solution of sodium carbonate (10% w/v, 1 ml) added.

After 1 hour at 90° C. the blue particles were washed and investigated with respect to their capacity to remove albumin from solution.

Thus, the particles were mixed with a solution of human plasma (~1 mg protein/ml) in 3% sodium chloride solution. After 20 minutes the particles were washed, the protein desorbed with an equal volume of 400 mM potassium thiocyanate in 1% sodium chloride solution and the soluble protein estimated by its adsorption at 280 nm. The $E_{10}^{280}$ value was 0.388. ($E_{10}^{280}$ is Optical Density at 280 nm in a 10 mm cell).

EXAMPLE 19

10 ml of a solution containing hydroxethyl methacrylate (1.1 ml) and bis acrylamide (0.015 g) in 0.1 M tris buffer (pH 7.5) were dry mixed with porous celite particles (15 ml) (of the kind used in Example 5). The mixture was deaerated and purged with nitrogen before being irradiated with 1 Megarad of γ-radiation. The particles were washed and found to contain 12.4% organic material.

A sample of the composite particles was treated with Cibachron Blue 3G-A as in Example 18.

The capacity of the particles to remove albumin from solution was tested as in Example 18 and the $E_{10}^{280}$ of the thiocyanate extract was ~0.181.

EXAMPLE 20

A sample of the composite prepared in Example 13 was treated with Cibachron Blue 3G-A as in Example 18 to give deep blue composite particles.

The albumin removal capacity of these particles was tested as in Example 18 and the $E_{10}^{280}$ of the thiocyanate extract was 0.100.

EXAMPLES 21 TO 24

These Examples relate to the production of ampholyte ion exchange composites.

Four solutions were used: polyethylene imine (BDH 10%) (Example 21) and three solutions containing polyethylene imine (BDH 10%) mixed in various ratios with monosodium glutamate (20%). (Examples 22-24).

5 ml samples of the four solutions were dry mixed with 8 ml samples of porous celite particles (of the kind used in Exampled 5) and a 1:1 mixture of acetone/50% glutaraldehyde (10 ml) was added. This localised the solution in the particles. The reaction proceeded for 8 hrs at 20° before the particles were washed and their ion exchange capacity determined by back titration with N hydrochloric acid. This capacity ranged from 3.5 mequivalents/ml of the mixture containing no glutamate to 2.5 meq/ml of one containing 3 parts glutamate to 1 part imine. The maximum buffering capacity for the ampholyte composites was as shown in the following table:

| Composite | | pH |
|---|---|---|
| Ex 21 - imine alone | | 5.5 |
| Ex 22 - 3 parts imine: | 1 part glutamate | 5.0 |
| Ex 23 - 1 part imine: | 1 part glutamate | 4.7 |
| Ex 24 - 1 part imine: | 3 parts glutamate | 2.7 |

EXAMPLE 25-29

Further ampholyte composites were prepared as follows:

Solutions of polyethylene imine (1 part) and monosidum glutamate (2 parts) were prepared with between 15% and 1.5% total dissolved solids. 6 ml of each solution was dry mixed with 9 ml of porous celite particles (of the kind used in Example 5) and reacted with 10 ml of 1:1 acetone/50% glutaraldehyde at 20° for 4 hours.

The ion-exchange capacity and protein absorbing capacity of the composite particles was investigated. Although the ion exchange capacity of the particles decreased with decreasing solids content the protein adsorbing capacity went through a maximum as illustrated by the data in the table below. This suggests that the 10% solids sample not only has microporosity for hydrogen ions but was macroporous and able to bind protein molecules.

The following table shows dissolved solids concentration of the starting solutions against the OD of a supernatant obtained after stirring the composite particles with 50 ml haemoglobin in tris-buffer (pH 8.3) (2 mg/ml).

| Example No. | % dissolved solids | OD of supernatant |
|---|---|---|
| 25 | 15 | 0.847 |
| 26 | 10 | 0.397 |
| 27 | 5 | 0.421 |
| 28 | 3 | 0.852 |
| 29 | 1.5 | 0.584 |

By way of comparison porous celite particles carrying no organic material gave a supernatant having an OD of 0.821.

EXAMPLE 30

An agarose compound was treated to impart ion exchange properties thereto.

Agarose/celite composite (prepared as in Example 5) (75 ml) was washed in 1 M sodium hydroxide and subsequently mixed with a solution of chloro-ethylamine hydrochloride (5 g) in 1 M sodium hydroxide to form a slurry. The slurry was heated to 90° for 2 hrs and then washed free of reagent.

The ability of the ion exchange composite material thus produced to bind haemoglobin was tested as in Example 1. The composite material bound twice as much haemoglobin as a control sample of celite.

EXAMPLE 31

An agrarose/celite composite as prepared in Example 6 was treated to introduce affinity chromatography properties thereto by covalent coupling of an affinity chromatography dye to the agarose.

Thus the composite material prepared (50 ml) as in Example 6 was washed and the supernatant solution decanted from the particles. A solution of Cibacron Blue 3 G-A dye (ex Ciba Giegy UK) (40 mg/ml, 20 ml) was mixed with the particles of composite material and the resulting slurry heated to 60° C.

Sodium chloride (5 g) was mixed with the slurry. After 15 minutes a 10% solution of sodium carbonate (10 ml) was added and the slurry heated to 90° C. for 1 hour.

The resulting blue composite of celite/agarose/Cibacron dye was washed with water and stored as an aqueous slurry.

EXAMPLE 32

A sample of composite material produced as in Example 14 was treated with Cibacron Blue 3G-A as in Example 18 to give blue composite particles. A sample of the composite particles were tested as in Example 18 with regard to albumin removal properties. The $E_{10}^{280}$ of the thiocyanate was 0.308.

EXAMPLE 33

A hot aqueous solution (290° C.) of agarose (4% w/v) was mixed with 50 ml porous celite particles (prepared in accordance with British Pat. No. 1,421,531 (U.S. Pat. No. 3,945,072) (250–425 $\mu$dia) until the porous particles were just filled (33 ml). The resulting mixture was maintained at 90° C. for 15 minutes before cooling to room temperature.

The agarose in the porous particles was cross-linked as follows:

A mixture was prepared by adding 10 ml epichlorhydrin to 50 ml of 1 M NaOH containing 5% v/v TWEEN 20 and emulsifying. 60 ml of this mixture was preheated to 60° C. and added to the agarose containing particles (preheated to 60° C.). After standing for 2½ hours at 60° C. with occasional stirring, the particles were washed until neutral pH was obtained.

The resulting particles of agarose/celite composite (shown by pyrolysis of a sample thereof to have a 3% by weight organic content) were treated to introduce affinity chromatography properties thereto by the covalent coupling of an affinity chromatography agent (Cibacron Blue 3GA dye) to the agarose.

Thus, after washing, as much water as possible was removed from the particles by decantation of the supernate and then they were heated to 90° C. 20 ml of 4% Cibacron Blue 3GA dye preheated to 90° C.) was added to the particles followed by 5 g of solid sodium chloride. After 15 minutes 10 ml of a 10% (w/v) sodium carbonate (preheated to 90° C.) was added and mixed and the resulting mixture left for 1 hour at 90° C. with occasional stirring.

The resultant dyed composite was allowed to cool, any aggregates were broken down by gentle sieving, and the particles washed to remove traces of excess dye.

EXAMPLE 34

The procedure of Example 33 was followed with the exceptions that the cross-linking procedure was omitted and the treatment with Cibacron Blue 3GA dye was conducted at 70° C. for 3 hours instead of 90° C. for 1 hour.

EXAMPLES 35–38

The procedure of Example 33 was followed with the exception that the concentration of the agarose starting solution was respectively 1% (Example 35), 2% (Example 36), 3% (Example 37) and 5% (Example 38).

EXAMPLES 39–42

The procedure of Example 34 was followed with the exception that the concentration of the agarose starting solution was respectively 1% (Example 39), 2% (Example 40), 3% (Example 41) and 5% (Example 42).

EXAMPLE 43

The albumin adsorption capacity of a sample of each of the composite materials produced as in Examples 35 to 42 was investigated and the results are presented in the following Table.

| Example No. | % agarose starting solution | Albumin Capacity* |
|---|---|---|
| 35 | 1 | 8.5 |
| 36 | 2 | 12.5 |
| 37 | 3 | 14.5 |
| 38 | 5 | 12.4 |
| 39 | 1 | 5.0 |
| 40 | 2 | 8.0 |
| 41 | 3 | 10.5 |
| 42 | 5 | 10.5 |

(*Albumin capacity is given in mg albumin/ml packed bed)

It will be appreciated that an increase in the concentration of agarose in the starting solution leads to an increase in agarose in the composite.

The albumin capacity was investigated in a manner similar to that set out in Example 10 of U.S. patent application of even date herewith claiming priority from British patent application No. 52434/76.

Reference may be made to this Application for details, but for convenience a brief description is given herein.

Thus, a given sample of composite material was packed into a column, washed and equilibrated, and subsequently human albumin was passed through the column whilst the Optical Density (OD) at 280 nm) of the eluate from column was monitored. When the OD indicated saturation of the column with albumin the column was washed and the albumin elute with KSCN solution.

The albumin capacity figures obtained indicate (i) (when plotted as a curve) that there is an optimum agarose concentration for albumin capacity at ~3% wt agarose in the composite (corresponding to a 4% w/v agarose starting solution) for both cross-linked and uncross-linked composite materials and (ii) the albumin capacity of composite material produced with cross-linking is higher than that of composite material produced without cross-linking.

U.S. patent application Ser. No. 858,749 of even date herewith, the disclosure of which is hereby incorporated by reference into this Specification, may be referred to for details of, inter alia, the separation of a chemical component from a fluid substance by use of a composite material having affinity chromatography properties in accordance with the present invention.

We claim:

1. A particulate material comprising a plurality of discrete porous rigid support particles, and a deformable xerogel retained within and substantially filling the pore structure of the support particles, said deformable xerogel comprising an affinity chromatography agent such that the particulate material is a composite material having affinity chromatography properties.

2. A particulate material according to claim 1 wherein said affinity chromatography agent comprises a group specific ligand capable of interacting specifically with the nucleotide binding sites of an enzyme.

3. A particulate material according to claim 1 wherein said affinity chromatography agent comprises a ligand capable of retaining proteins from human plasma.

4. A particulate material according to claim 1 wherein said deformable xerogel comprises a polysaccharide gel or a synthetic polymer gel.

5. A particulate material according to claim 4 wherein said polysaccharide gel is an agarose gel or a cellulose gel.

6. A particulate material according to claim 4 wherein said synthetic polymer gel is a polymer of an acrylate or a polyvinyl alcohol polymer gel.

7. A method for preparing a particulate material comprising a deformable xerogel retained in the pore structure of a particulate porous rigid support material which comprises introducing a precursor for the xerogel into the pore structure of a plurality of discrete particles of porous rigid support material such that the gel precursor fills the pores of the discrete particles, and effecting gelation of the precursor within the discrete particles to form a plurality of discrete porous rigid support particles having a deformable xerogel retained within and substantially filling the pore structure of the support particles, said deformable xerogel having affinity chromatography properties.

8. A method for preparing a particulate material comprising a deformable xerogel retained in the pore structure of a particulate porous rigid support material which comprises introducing a precursor for the xerogel into the pore structure of a plurality of discrete particles of porous rigid support material such that the gel precursor fills the pores of the discrete particles, and effecting gelation of the precursor within the discrete particles to form a plurality of discrete porous rigid support particles having a deformable xerogel retained within and substantially filling the pore structure of the support particles, and treating the deformable xerogel retained within the pores of said rigid support material to impart affinity chromatography properties to the deformable xerogel.

9. A method according to claim 8 wherein said treating step comprises coupling an affinity chromatography ligand to the deformable xerogel.

* * * * *